United States Patent [19]
Kato et al.

[11] Patent Number: 4,822,567
[45] Date of Patent: Apr. 18, 1989

[54] ANTIBIOTIC ALLOYS

[75] Inventors: Isamu Kato, Toyonaka; Sadayuki Yuhda, Suita; Naoki Oda, Nishinomiya; Masahiro Suganuma, Suita, all of Japan

[73] Assignee: Sankin Kogyo Kabushiki Kaisha, Osaka, Japan

[21] Appl. No.: 113,908

[22] Filed: Oct. 29, 1987

[30] Foreign Application Priority Data

Nov. 7, 1986 [JP] Japan .................. 61-266438

[51] Int. Cl.$^4$ .............. C22C 38/10; C22C 19/00; C22C 30/00
[52] U.S. Cl. ..................... 420/95; 420/104; 420/435; 420/436; 420/440; 420/585; 420/441; 420/452; 420/457; 420/458; 420/459; 420/442
[58] Field of Search ............ 420/435, 436, 440, 441, 420/442, 452, 454, 457, 459, 458, 581, 583, 585, 95, 107, 104; 148/425; 433/207, 208, 201.1, 228.1, 18, 2, 8; 106/35

[56] References Cited

U.S. PATENT DOCUMENTS

| | | | |
|---|---|---|---|
| 1,862,559 | 6/1932 | White et al. | 420/440 |
| 4,014,691 | 3/1977 | Mohammed | 420/436 |
| 4,108,642 | 8/1978 | Chiaramonte | 420/452 |
| 4,491,561 | 1/1985 | Mann | 420/437 |

FOREIGN PATENT DOCUMENTS

| | | | |
|---|---|---|---|
| 4633382 | 9/1981 | Japan | 420/440 |
| 59-50145 | 3/1984 | Japan | 420/440 |

Primary Examiner—Deborah Yee
Attorney, Agent, or Firm—Oblon, Fisher, Spivak, McClelland & Maier

[57] ABSTRACT

Antibiotic alloys adapted for making sanitary articles, such as orthodontic fittings and component parts of water purifying apparatus, the alloy containing cobalt to impart an antibiotic ability hereto, and iron and nickel to enhance the workability thereof so that the alloy can be easily worked into intricate shapes.

9 Claims, 1 Drawing Sheet

ANTIBIOTIC ALLOYS

BACKGROUND OF THE INVENTION

1. Field of the Invention

The present invention relates to an antibiotic alloy, and more particularly to an antibiotic alloy having such workability that it is easily worked into intricate shapes of orthodontic fittings, such as othodontic brackets and bands, mesh bonding pads, deciduous crowns. The alloys of the present invention is also applicable to the production of fibrous alloys and mechanical component parts which must be kept hygienic, such as parts of water purifying apparatus. In the following description the orthodontic fittings will stand for all applicable articles.

2. Description of Prior Art

It is well known in the dental field to employ orthodontic bands and brackets for correcting occlusal disharmony. They are fitted between or around patient's teeth and gums over a year or more. However they are likely to provide a bed for bacteria to grow therein which causes caries in the teeth.

As a result, after the occlusal disharmony has been corrected another treatment is required for the caries in the tooth. The achieved dental harmony will be traded off by the spoiled decayed teeth. This leads to the economical waste for the patient.

OBJECTS AND SUMMARY OF THE INVENTION

The present invention aims at solving the problems pointed out above, and has for its object to provide an antibiotic alloy adapted for making sanitary articles, such as orthodontic fittings.

Another object of the present invention is to provide an antibiotic alloy which is improved in workability so that it is easily worked into intricate shapes of sanitary articles, such as orthodontic fittings.

Other objects and advantages of the present invention will become more apparent from the following detailed description, when taken in conjunction with the accompanying drawing which shows, for the purpose of illustration only, one embodiment in accordance with the present invention.

According to the present invention there is provided an antibiotic alloy improved in workability, containing Co, Fe, Ni and unavoidable impurities, wherein the metallic contents are in the following range:

$30\% \leq 3.0\text{Fe} + \text{Ni}$ $\text{Fe} + \text{Ni} \leq 58\%$ $\text{Co} \geq 42\%$ The inventors have discovered that the Co layer overlaid on an orthodontic fitting is capable of killing bacteria in the vicinity of the fitting. However, they have experienced that the cobalt-covered metal is difficult to work into such intricate shapes as those of orthodontic fittings. To improve this drawback the inventors have thought it out to alloy cobalt, iron and nickel. As a result the workability of the alloy has been enhanced without trading off its antibiotic merit.

DETAILED DESCRIPTION OF THE PREFERRED EMBODIMENT

Figure 1:
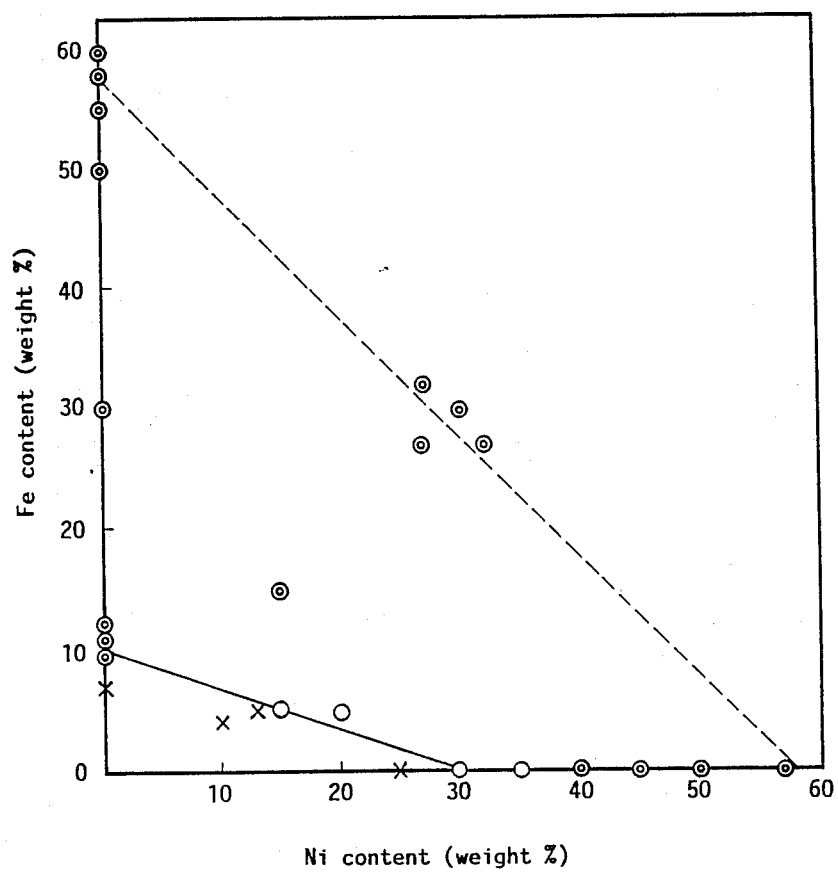
FIG. 1 is a graph showing proportions of Fe and Ni contents to be added in the alloy.

The present invention will now be described in detail with specific reference to the following example:

Thirty-one discs (No. 1 to No. 31) were made of alloys, wherein each alloy contains Co, Fe, Ni, Cr, Cu, Si and Mn in different proportion from others as shown in Table 1. However they have the same thickness (1 mm) and diameter (10 mm). The discs were placed on a culture medium in which *streptococcus mutans* K1R, IB, BHT, FA1 and OMZ176 grew. Bacteria-free circles appearing in each disc were individually observed as shown in Table 1, wherein the marks A, B and C in the column indicate evaluations with respect to anti-color change:

A: No color change occurred;

B: Slight color change occurred but it is to an applicable degree;

C: Remarkable color change occurred to an impracticable degree.

TABLE 1

| No. | Co | Fe | Ni | Cr | Cu | Si | Mn | Workability | Bacteria-Free Circle | Color Change |
|---|---|---|---|---|---|---|---|---|---|---|
| 1 | 88.5 | 7 | — | 4 | — | 0.5 | — | P | G | A |
| 2 | 84.5 | 10 | — | 5 | — | 0.5 | — | G | G | A |
| 3 | 82.5 | 12 | — | 3 | 2 | 0.5 | — | E | G | B |
| 4 | 63.2 | 30 | — | 2 | 4 | 0.8 | — | E | G | B |
| 5 | 47.3 | 50 | — | 2 | — | 0.6 | 0.1 | E | G | B |
| 6 | 37.3 | 58 | — | 4 | — | 0.6 | 0.1 | E | P | A |
| 7 | 37.3 | 60 | — | 2 | — | 0.6 | 0.1 | E | P | B |
| 8 | 42 | 58 | — | — | — | — | — | E | G | C |
| 9 | 45 | 55 | — | — | — | — | — | E | G | C |
| 10 | 79.5 | 11 | — | 3 | 6 | 0.5 | — | E | P | B |
| 11 | 63.2 | 30 | — | 6 | — | 0.8 | — | E | P | A |
| 12 | 70.5 | — | 25 | 4 | — | 0.5 | — | P | G | A |
| 13 | 60.5 | — | 35 | 4 | — | 0.5 | — | G | G | A |
| 14 | 55.5 | — | 40 | 4 | — | 0.5 | — | E | G | A |
| 15 | 46.8 | — | 45 | 4 | 3 | 1.2 | — | E | G | A |
| 16 | 47.5 | — | 50 | 2 | — | 0.4 | 0.1 | E | G | B |
| 17 | 43 | — | 57 | — | — | — | — | E | G | C |
| 18 | 39.5 | — | 58 | 2 | — | 0.4 | 0.1 | E | P | B |
| 19 | 42 | — | 58 | — | — | — | — | E | G | C |
| 20 | 53.8 | — | 35 | 4 | 6 | 1.2 | — | G | P | A |
| 21 | 66.7 | 15 | 15 | 3 | — | 0.3 | — | E | G | B |
| 22 | 76.7 | 5 | 15 | 3 | — | 0.3 | — | G | G | B |
| 23 | 78.7 | 5 | 13 | 3 | — | 0.3 | — | P | G | B |
| 24 | 82.7 | 4 | 10 | 3 | — | 0.3 | — | P | G | B |
| 25 | 75 | 5 | 20 | — | — | — | — | G | G | C |
| 26 | 35 | 30 | 30 | 4 | — | 1 | — | E | P | A |

TABLE 1-continued

| No. | Co | Fe | Ni | Cr | Cu | Si | Mn | Workability | Bacteria-Free Circle | Color Change |
|---|---|---|---|---|---|---|---|---|---|---|
| 27 | 39 | 27 | 32 | 1.5 | — | 0.5 | — | E | P | B |
| 28 | 44 | 27 | 27 | 1.5 | — | 0.5 | — | E | G | B |
| 29 | 39 | 32 | 27 | 1.5 | — | 0.5 | — | E | P | B |
| 30 | 70 | 30 | — | — | — | — | — | G | G | C |
| 31 | 70 | — | 30 | — | — | — | — | G | G | C |

(Note)
E: Excellent
G: Good
P: Poor

It was found out that the addition of a small portion of Si and Mn imparted a sufficient deoxidizing ability to each specimen. However, when the quantities of Si and Mn exceeded 2% and 3%, respectively, the specimens were too fragile to work them into intricate shapes.

As described above the antibiotic alloy of the present invention contains Fe and Ni addition to Co so that the alloys have enhanced workability as well as antibiotic ability. Each effect achieved by the alloys will be hereinafter described in detail:

Antibiotic ability

Plaques are likely to occur around orthodontic fittings embedded in the teeth. *Streptococcus mutans*, which are known to decay teeth, feed on the plaque and grow to produce an oxidizing agent, which degrades the pH value of the fittings. Under the present invention the cobalt contained in the alloy exhibits antibiotic ability for the bacteria; that is, since the pH value decreases in accordance with an increase in the number of *streptococcus mutans* the cobalt ions are generated to prevent the growth of the bacteria.

It has been found out through experiments that if the Co content is less than 42% the alloy is effective to prevent the mutans from growing because of a sufficient elution of Co ions so long as the pH value of and around the fittings is not larger than 6. Normally the pH value in the mouth is 6.5 to 7.0, where the elution of Co will not occur. However, as the mutans grow in the mouth the Co contained in the fittings exhibits the following merits:

When the pH value becomes 6.0 or less the Co ions start to elude if the content of Co not small than 42%. Otherwise it is difficult to secure a sufficient elution of Co ions to prohibit the mutans from growing; in other words, it means that the contents of Fe and Ni must be not larger than 58%. In FIG. 1 the dotted lines indicate the requirements for achieving an optimum conditions. The symbols in the graph of FIG. 1 have the following meanings:

◉ means E (excellent)
◉ indicates the reduction rate is 50% or more
○ means G (good)
○ indicates that the reduction is in the range of less than 50% to 20%
X means P (poor)
X indicates that the reduction is less than 20%.

It is important to note that the elution of Co ions does not occurs at any time but does only at a critical point when the mutans has grown to decay the teeth. The enamelum of the teeth begins to solve when the pH value becomes 5.2 or less. Advantageously the Co begins to elude at the pH of 6.0 or less. It is generally known that if too many Co ions elude they are likely to provide health hazard. However it has been demonstrated by using artificial saliva that the elution in the saliva does not reach such an amount as to cause health hazard.

Workability

It is generally known that an alloy must be reduced in size by at least 20% under pressure when it is used to make dental articles having intricate shapes such as orthodontic fittings. However it has been found that an alloy containing cobalt cannot meet this requirement. Therefore iron and nickel are added in the proportion of (Fe+Ni≦58%). Table 1 shows that the workability depends upon the proportion of Fe and Ni; in Table 1 "E (excellent)" indicates the reduction rate is 50% or more, "G (good)" indicates that it is in the range of 50% (excluding 50%) to 20%, and "P (poor)" indicates that it is less than 20%. On the basis of the results obtained through the experiments the following formula is obtained to determine an optimum range of Fe and Ni:

$$30\% \leqq 3.0\text{Fe} + \text{Ni}$$

wherein the Fe and Ni indicate percentages of these elements.

In addition to Fe and Ni Cr and/or Cu may be added to enhance the anti-corrosion ability if each content does not exceed 5%. Cr and Cu are effective to protect the alloy against becoming reddish due to the corrosion of cobalt. However if either of Cr or Cu exceeds 5% the anti-corrosion ability works too strongly to allow the Co ions from eluding when the pH in the mouth reaches a determined value.

Si and Mn are added to prevent the Fe and Co contents in the alloy from becoming oxidized when the alloy is worked into orthodontic fittings at factories. The quantities of them are in the manufacturers' common knowledge.

What is claimed is:

1. An antibiotic alloy adapted for orthodontic fittings and sanitary articles whose antibacterial properties result from the leaching of cobalt from the alloy, consisting essentially of: cobalt, iron and nickel in amounts within the confines of the relationships expressed below, and from 1.5 to 5% of Cr, from 2% to 5% of Cu, or combinations thereof, and the unavoidable impurities $$30\% \leqq 3.0\text{Fe} + \text{Ni}$$
$$\text{Fe} + \text{Ni} \leqq 58\%$$
$$\text{Co} \geqq 42\%.$$

2. An antibiotic alloy adapted for orthodontic fittings and sanitary articles whose antibacterial properties result from the leaching of cobalt from the alloy, consisting essentially of: cobalt, iron and nickel in amounts consistent with the relationships expressed below, and from 0.3% to 3% Si, from 0.1 to 2% Mn, or a combination thereof and the unavoidable impurities:

$$30\% \leqq 3.0\text{Fe} + \text{Ni}$$
$$\text{Fe} + \text{Ni} \leqq 58\%$$
$$\text{Co} \geqq 42\%.$$

3. The antibiotic alloy as set forth in claim 1, wherein the orthodontic fittings are brackets and bands for correcting occulusal disharmony, deciduous crowns, and mesh bonding pads.

4. An antibiotic alloy as set forth in claim 1, wherein the santiary articles include materials for making fibrous alloys.

5. The antibiotic alloy as set forth in claim 1, wherein the sanitary articles are component parts of water purifying apparatus.

6. An antibiotic alloy adapted for orthodontic fittings and sanitary articles whose antibacterial properties result from the leaching of cobalt from the alloy, consisting essentially of: cobalt, iron and nickel in amounts within the confines of the relationships expressed below, from 1.5 to 5% of Cr and from 2% to 5% of Cu, and the unavoidable impurities $30\% \leq 3.0Fe + Ni$
$Fe + Ni \leq 58\%$
$Co \geq 42\%$.

7. an antibiotic alloy adapted for orthodontic fittings and sanitary articles whose antibacterial properties result from the leaching of cobalt from the alloy, consisting essentially of: cobalt, iron and nickel in amounts within the confines of the relatioships expressed below, from 1.5 to 5% of Cr, from 2% to 5% of Cu, from 0.3 to 3% Si and from 0.1 to 2% Mn, and the unavoidable impurities $30\% \leq 3.0Fe + Ni$
$Fe + Ni \leq 58\%$
$Co \geq 42\%$.

8. An antibiotic alloy adapted for orthodontic fittings and sanitary articles whose antibacterial properties result from the leaching of cobalt from the alloy, consisting essentially of: cobalt, iron and nickel in amounts within the confines of the relationships expressed below, from 1.5 to 5% of Cr, from 0.3 to 3% Si and from 0.1 to 2% Mn, and the unavoidable impurities $30\% \leq 3.0Fe + Ni$
$Fe + Ni \leq 58\%$
$Co \geq 42\%$.

9. An antibiotic alloy adapted for orthodontic fittings and sanitary articles whose antibacterial properties result from the leaching of cobalt from the alloy, consisting essentially of: cobalt, iron and nickel in amounts within the confines of the relationships expressed below, from 2% to 5% of Cu, from 0.3 to 3% Si and from 0.1 to 2% Mn, and the unavoidable impurities $30\% \leq 3.0Fe + Ni$
$Fe + Ni \leq 58\%$
$Co \geq 42\%$.

* * * * *